(12) United States Patent
Ma et al.

(10) Patent No.: US 12,741,935 B2
(45) Date of Patent: Sep. 22, 2026

(54) PROCESS FOR MAKING TAURINE

(71) Applicant: Archer Daniels Midland Company, Decatur, IL (US)

(72) Inventors: Chi Cheng Ma, Champaign, IL (US); James Brazdil, Leland, NC (US); Hao Luo, Decatur, IL (US)

(73) Assignee: ARCHER-DANIELS-MIDLAND COMPANY, Decatur, IL (US)

(*) Notice: Subject to any disclaimer, the term of this patent is extended or adjusted under 35 U.S.C. 154(b) by 685 days.

(21) Appl. No.: 18/002,329

(22) PCT Filed: Jun. 18, 2021

(86) PCT No.: PCT/US2021/038112
§ 371 (c)(1),
(2) Date: Dec. 19, 2022

(87) PCT Pub. No.: WO2021/258005
PCT Pub. Date: Dec. 23, 2021

(65) Prior Publication Data

US 2023/0348370 A1 Nov. 2, 2023

Related U.S. Application Data

(60) Provisional application No. 63/041,519, filed on Jun. 19, 2020.

(51) Int. Cl.
*C07C 309/14* (2006.01)

(52) U.S. Cl.
CPC .................................. *C07C 309/14* (2013.01)

(58) Field of Classification Search
None
See application file for complete search history.

(56) References Cited

U.S. PATENT DOCUMENTS 2,693,488 A * 11/1954 Sexton .................... B01J 39/00 562/104
4,657,704 A * 4/1987 Yamamoto ........... C07C 303/02 562/107
2015/0183731 A1* 7/2015 Hu ....................... C07C 303/02 558/23

OTHER PUBLICATIONS

Plutschack ("The Hitchhiker's Guide to Flow Chemistry" Chemical Reviews, 2017, p. 111796) (Year: 2017).*

(Continued)

*Primary Examiner* — Amy C Bonaparte
(74) *Attorney, Agent, or Firm* — Andrew F. Nilles

(57) ABSTRACT

A process is described for forming taurine, which comprises reacting monoethanolamine with sulfuric acid to provide an 2-aminoethanol hydrogen sulfate ester product, combining the 2-aminoethanol hydrogen sulfate ester product with at least one of carbon dioxide, a carbonate or bicarbonate and with at least one of a sulfite or bisulfite to form a sulfonation reaction mixture, and heating the sulfonation reaction mixture for a sufficient time to form a taurine product therefrom. The efficiency of the sulfonation step is improved sufficiently to enable a continuous process for making taurine, particularly with at least some concurrent water removal in the first, esterification step to facilitate full conversion of the monoethanolamine to the desired 2-aminoethanol hydrogen sulfate ester intermediate.

18 Claims, 7 Drawing Sheets

(56) References Cited

OTHER PUBLICATIONS

Carbon Dioxide ("5.5 Dissolved Gases: Carbon Dioxide, pH, and Ocean Acidification", downloaded from https://rwu.pressbooks.pub/webboceanography/chapter/5-5-dissolved-gases-carbon-dioxide-ph-and-ocean-acidification/ on Jun. 25, 2025) (Year: 2025).*

* cited by examiner

TABLE 4

| Sample# | Sodium sulfite / AES (molar) | Sodium bisulfite / AES (molar) | Carbonate / AES (molar) | NaOH / Sodium bisulfite (molar) | Temp. (°C) | Reaction time (h) | AES conv. | MEA yield (molar) | Free Taurine yield (molar) | 2-(Carboxy amino)ethane sulfonic acid yield (molar) | Total Taurine yield (molar) - (Free Taurine + 2-(Carboxy amino) ethane sulfonic acid, converted to taurine) | N-2-Aminoethyl-2-aminoethane sulfonic acid (molar) |
|---|---|---|---|---|---|---|---|---|---|---|---|---|
| 1 | | 1.3 | 0.1 | 1 | 130 | 2 | 93.5 | 8.6 | 76.1 | 4.1 | 80.2 | ** |
| 2 | | 1.2 | 0.1 | 1 | 130 | 2 | 93.3 | 9.5 | 76.4 | 2.7 | 79.1 | ** |
| 3* | | 1.3 | 0 | 1 | 130 | 2 | 89.5 | 8.0 | 60.2 | 0 | 60.2 | 23 |
| 4 | | 1.35 | 0.48 | 0.49 | 150 | 1 | 100.0 | 14.4 | 65.9 | 5.9 | 71.8 | <1 |
| 5 | | 1.36 | 0.55 | 0.56 | 150 | 1 | 100.0 | 13.7 | 60.5 | 11.1 | 71.6 | <1 |
| 6 | | 1.36 | 0.59 | 0.61 | 150 | 1 | 100.0 | 17.0 | 58.0 | 16.2 | 74.2 | <1 |
| 7 | | 1.36 | 0.58 | 0.72 | 150 | 1 | 100.0 | 17.1 | 57.1 | 18.4 | 75.5 | <1 |
| 8 | | 1.35 | 0.80 | 0.77 | 150 | 1 | 100.0 | 17.3 | 52.6 | 28.9 | 81.5 | <1 |
| 9 | | 1.36 | 0.88 | 0.77 | 150 | 1 | 100.0 | 17.7 | 50.7 | 29.4 | 80.1 | <1 |
| 10 | | 1.35 | 0.96 | 0.78 | 150 | 1 | 100.0 | 18.2 | 55.7 | 23.9 | 79.6 | <1 |
| 11 | | 1.22 | 0.81 | 0.71 | 150 | 1 | 100.0 | 18.3 | 45.4 | 28.1 | 73.5 | <1 |
| 12 | | 1.34 | 0.70 | 0.8 KOH | 150 | 1 | 100.0 | 17.9 | 55.1 | 24.9 | 80.0 | <1 |
| 13 | | 1.22 | 0.81 | 0.71 | 150 | 1 | 100.0 | 20.7 | 47.3 | 28.1 | 75.4 | <1 |
| 14* | 1.29 | 0 | 0 | 0 | 150 | 1 | 100.0 | 11.0 | 64.2 | 0 | 64.2 | ** |
| 15 | | 1.22 | 0.74 | 0.73 | 150 | 1 | 100.0 | 21.8 | 52.7 | 22.8 | 75.5 | <1 |
| 16 | | 1.36 | 0.47 | 0.94 | 150 | 1 | 100.0 | 21.4 | 59.1 | 18.2 | 77.3 | <1 |
| 17 | | 1.37 | 0.46 | 0.88 | 150 | 1 | 100.0 | 20.0 | 60.8 | 15.0 | 75.8 | <1 |
| 18 | | 1.11 | 0.43 | 0.70 | 150 | 1 | 100.0 | 22.7 | 57.7 | 12.1 | 69.8 | <1 |
| 19 | | 0.92 | 0.42 | 0.56 | 150 | 1 | 100.0 | 15.1 | 52.8 | 6.7 | 59.5 | <1 |
| 20 | | 1.31 | 0.10 | 1.01 | 130 | 2 | 93.5 | 8.6 | 76.1 | 4.1 | 80.2 | 5.92 |
| 21 | | 1.31 | 0.10 | 1.00 | 130 | 2 | 93.3 | 9.5 | 76.4 | 2.7 | 79.1 | 5.04 |
| 22 | | 1.32 | 0.10 | 1.01 | 130 | 2 | 95.5 | 10.8 | 73.6 | 3.3 | 76.9 | 5.96 |
| 23 | | 1.32 | 0.10 | 0.90 | 130 | 2 | 89.4 | 9.0 | 71.4 | 3.1 | 74.5 | 5.68 |
| 24 | | 1.32 | 0.10 | 0.81 | 130 | 2 | 86.1 | 9.3 | 66.3 | 3.7 | 70.0 | 4.93 |
| 25 | 1.22 | 0 | 0.22 | 0 | 130 | 2 | 97.3 | 10.7 | 75.1 | 5.2 | 80.3 | 3.77 |
| 26 | | 1.32 | 0.11 | 0.80 | 140 | 2 | 94.4 | 10.8 | 72.4 | 1.0 | 73.4 | 6.85 |
| 27 | | 1.31 | 0.11 | 0.92 | 140 | 2 | 98.1 | 13.1 | 76.9 | 1.7 | 78.6 | 6.86 |
| 28 | 1.21 | 0 | 0.22 | 0 | 140 | 2 | 100.0 | 11.6 | 69.9 | 7.3 | 77.2 | 7.99 |

FIG. 6

| | | | | | | | | | | | | |
|---|---|---|---|---|---|---|---|---|---|---|---|---|
| 29 | | 1.32 | 0.11 | 1.05 | 140 | 2 | 100.0 | 10.0 | | ** | 72.6 | ** |
| 30 | | 1.31 | 0.11 | 0.96 | 140 | 2 | 100.0 | 10.0 | | ** | 74.7 | ** |
| 31 | | 1.32 | 0.11 | 0.95 | 150 | 1 | 100.0 | 10.0 | | ** | 62.9 | ** |
| 32 | | 1.32 | 0.11 | 1.01 | 130 | 2 | 100.0 | 11.6 | | ** | 80.5 | ** |
| 33 | | 1.31 | 0.11 | 0.79 | 140 | 2 | 97.1 | 11.7 | 65.3 | 2.4 | 67.7 | ** |
| 34 | | 1.33 | 0.11 | 1.01 | 140 | 2 | 100.0 | 10.0 | 69.1 | 8.6 | 77.7 | ** |
| 35 | | 1.32 | 0.11 | 1.02 | 150 | 1 | 100.0 | 13.0 | 65.0 | 9.8 | 74.8 | ** |
| 36 | | 1.31 | 0.22 | 0.94 | 150 | 1 | 100.0 | 16.4 | 70.1 | 8.6 | 78.7 | ** |
| 37 | | 1.32 | 0.23 | 1.04 | 150 | 1 | 96.2 | 16.3 | 68.4 | 8.4 | 76.8 | ** |
| 38 | | 1.31 | 0.22 | 0.96 | 140 | 2 | 100.0 | 11.6 | 65.1 | 7.9 | 73.0 | ** |
| 39 | | 1.32 | 0.23 | 1.04 | 140 | 2 | 100.0 | 12.6 | 72.0 | 8.2 | 80.2 | ** |
| 40 | | 1.37 | 0.60 | 0.61 | 150 | 1 | 100.0 | 17.3 | 68.8 | 12.7 | 81.5 | ** |
| 41 | | 1.37 | 0.60 | 0.66 | 150 | 1 | 100.0 | 16.4 | 63.8 | 16.5 | 80.3 | ** |
| 42 | | 1.37 | 0.69 | 0.51 | 150 | 1 | 100.0 | 12.3 | 68.8 | 12.2 | 81.0 | ** |
| 43 | | 1.36 | 0.64 | 0.57 | 150 | 1 | 100.0 | 18.2 | 71.4 | 10.6 | 82.0 | ** |

* Control (no carbonate addition)

** Was not measured

FIG. 6 (continued)

PROCESS FOR MAKING TAURINE

CROSS-REFERENCE TO RELATED APPLICATIONS

This application is a national stage entry of International Application No. PCT/US21/038112, filed Jun. 18, 2021, which itself claims priority to U.S. Provisional Patent Application No. 63/041,519, filed Jun. 19, 2020, each of the contents of the entirety of which are incorporated by this reference.

FIELD OF INVENTION

This invention relates to a continuous process for producing taurine from aminoethanol sulfate ester, also called 2-aminoethanol hydrogen sulfate ester (AES).

BACKGROUND OF THE INVENTION

Taurine, also known as 2-aminoethanesulfonic acid, is an amino acid that is found in natural dietary sources, biosynthesized in the body and is also produced by chemical synthesis for commercial purposes. Taurine is sometimes referred to as a conditional amino acid because it is derived from cysteine like other amino acids but lacks a carboxyl group that usually belongs to amino acids. Instead, it contains a sulfide group and can be called an amino sulfonic acid.

The world's annual consumption of taurine has been more than 50,000 tons, of which more than 80% are used as food and nutrition additives. Two methods have been used commercially to produce taurine, one method having ethylene oxide (EO) as starting material, and the other method having monoethanolamine (MEA) as starting material.

In the EO method, EO is reacted with sodium bisulfite to produce sodium isethionate, which is then converted via ammonolysis to sodium taurinate. Sodium taurinate is then neutralized to produce taurine. When sodium taurinate is neutralized with sulfuric acid, then a mixture of taurine and sodium sulfate is obtained. As disclosed in U.S. Pat. No. 8,609,890, sodium taurinate may be neutralized with sulfur dioxide to obtain taurine and to regenerate sodium bisulfite.

As disclosed in U.S. Pat. No. 9,145,359, one disadvantage of the EO method lies in the problematic quality of the product. More specifically, taurine produced via the EO method is a powder, and tends to form a hard cake over a short period of time during storage (in a matter of weeks), possibly due to the presence of unknown impurities. The process also involves some serious hazards from the viewpoint of safety since it uses ethylene oxide as a raw material, and ethylene oxide has extremely strong toxicity and carcinogenicity as well as posing considerable safety risks in its transport and handling. Moreover, the reaction from EO is carried out at very high temperatures (220-280° C.) and pressures (>100 bars).

In a conventional method using MEA as the starting material, taurine can be prepared by reacting MEA with sulfuric acid to obtain the intermediate 2-aminoethanol hydrogen sulfate ester (AES) and then sulfonating this ester intermediate. The MEA method uses a much safer starting material and produces a needle-shaped crystalline taurine product with excellent stability during transportation and storage as compared to the taurine powder produced in the EO method. A further advantage is the mild processing conditions as compared to the high temperature and pressures as required in the EO method.

A disadvantage of the MEA method on the other hand has been its higher cost of manufacture and higher capital expenditures, as compared to the EO method.

A further disadvantage of the MEA method is the lengthy time required for the sulfonation stage, typically from 35-40 hours, due to the slow reaction of AES and sodium sulfite. The MEA method also typically has a low product yield in the sulfonation step.

U.S. Pat. No. 9,145,359 discloses a method for the production of taurine by a cyclic process of reacting monoethanolamine, sulfuric acid, and ammonium sulfite in the presence of additives to inhibit the hydrolysis of 2-aminoethanol hydrogen sulfate ester (AES) intermediate. The patent states that the hydrolysis of AES is accelerated under both acidic and basic conditions, and contends that the yield of taurine can be drastically increased by strictly maintaining the pH of the reaction mixture from 6.0 to 8.0 and carrying out the sulfonation reaction at a temperature of 80 to 150° C. The patent discloses examples wherein starting materials were reacted in an autoclave equipped with a stirrer for 24 hours at 110° C. under autogenous pressure for 24 hours, and examples wherein starting materials were reacted in the same autoclave for 18 hours at 120° C.

U.S. Pat. No. 10,131,621 has the same named inventor as U.S. Pat. No. 9,145,359. U.S. Pat. No. 10,131,621 discloses an extraction process for recovering aminoalcohols and glycols from aqueous streams of taurine production. The aqueous streams which contain aminoalcohols and/or glycols are first mixed with a base to increase pH and then extracted with $C_3$-$C_6$ alcohols, ketones, and ethers. The aqueous streams are then returned to their respective cyclic process for the production of taurine. The patent states that according to the MEA process disclosed in U.S. Pat. No. 9,145,359, (i) monoethanolamine is reacted first with sulfuric acid to afford 2-aminoethanol hydrogen sulfate ester, which undergoes a sulfonation reaction with ammonium sulfite to yield a mixture of taurine and ammonium sulfate, and (ii) during the sulfonation reaction, up to 15% of the intermediate ester is hydrolyzed to monoethanolamine, which is left in the waste stream as its sulfate salt, along with ammonium sulfite and ammonium sulfate, or along with sodium sulfite and sodium sulfate when sodium sulfite is used as sulfonation agent.

Typical EO and MEA methods are both batch type processes that do not allow for continuous production of taurine.

It would be beneficial to have processes and products that do not have the disadvantages of these conventional methods. For example, it would be beneficial to have a continuous process that produces a stable crystalline taurine product. It would further be beneficial to have a continuous process that that produces stable crystalline taurine in a shorter period of time than the batch sulfonation stage of conventional MEA methods.

BRIEF SUMMARY OF THE INVENTION

In a first aspect, the present invention relates to a process for making taurine, comprising forming 2-aminoethanol hydrogen sulfate ester in a first, esterification step by reacting monoethanolamine with sulfuric acid, then sulfonating the 2-aminoethanol hydrogen sulfate ester from the first, esterification step by reaction with a sulfite, bisulfite or combination of these in the presence of carbon dioxide, a carbonate, bicarbonate or a combination of any of these in a second, sulfonation step to produce a taurine product.

In a further, preferred aspect, the present invention relates to a continuous process for making taurine, wherein the first, esterification step is carried out continuously with some concurrent water removal to produce a continuous 2-aminoethanol hydrogen sulfate ester feed for the second, sulfonation step, and the second, sulfonation step is also carried out directly and continuously on this 2-aminoethanol hydrogen sulfate ester feed from the first, esterification step.

In certain embodiments of the second, sulfonation step, the molar ratio of the sulfite, bisulfite or combination thereof to the 2-aminoethanol hydrogen sulfate ester is equal to or greater than 1.0 and less than about 3.0, preferably less than 2.0, more preferably less than 1.8, and even more preferably less than 1.5.

In certain embodiments of the second, sulfonation step, the molar ratio of the carbon dioxide. carbonate, bicarbonate or combination of any of these to the 2-aminoethanol hydrogen sulfate ester is equal to or greater than 0.1 and less than 1.0.

In certain embodiments of the second, sulfonation step, a first stream, a second stream and a third stream are added to a sulfonation vessel, wherein the first stream comprises 2-aminoethanol hydrogen sulfate ester, the second stream is chosen from carbon dioxide, a carbonate, a bicarbonate or a combination of any of these, and the third stream comprises an aqueous solution of at least one of a sulfite, a bisulfite or a combination of these, and the combined first, second and third streams are subjected to heat in the presence of an inert gas such that taurine is formed.

In certain embodiments of the first, esterification step, the concurrent water removal involved in that step will be at least in part accomplished by contact with an inert particulate material during the esterification step which possesses the capability of receiving and removing water from the process as it is formed, then in these embodiments removing the inert particulate material to provide a 2-aminoethanol hydrogen sulfate ester product for the second, sulfonation step.

In certain other embodiments, the concurrent water removal is accomplished at least in part by introduction of a feed comprising at least some monoethanolamine and at least some sulfuric acid into a spray dryer or thin film evaporator, and reacting the at least some monoethanolamine and the at least some sulfuric acid while using spray drying or thin film evaporation to remove water from the process.

In still other embodiments, the concurrent water removal is accomplished at least in part by use of the inert particulate material with also carrying out some of the esterification within a spray dryer or thin film evaporator, In certain of these "combined water removal mode" embodiments, the spray drying or thin film evaporation follows some reaction of monoethanolamine with sulfuric acid in the presence of the inert particulate material to form 2-aminoethanol hydrogen sulfate ester, while in other embodiments the reaction of monoethanolamine with sulfuric acid in the presence of the inert particulate material is carried out substantially in the spray dryer or thin film evaporator.

Preferably, the water removal accomplished in the first, esterification step by any means or combination of means will be sufficient to enable full conversion to the desired 2-aminoethanol hydrogen sulfate ester intermediate.

These and other aspects, embodiments, and associated advantages will become apparent from the following Detailed Description.

BRIEF DESCRIPTION OF THE DRAWINGS

FIG. 6 provides a tabulation of results from a number of Examples reported below.

DETAILED DESCRIPTION OF ILLUSTRATIVE EMBODIMENTS

Figure 1:
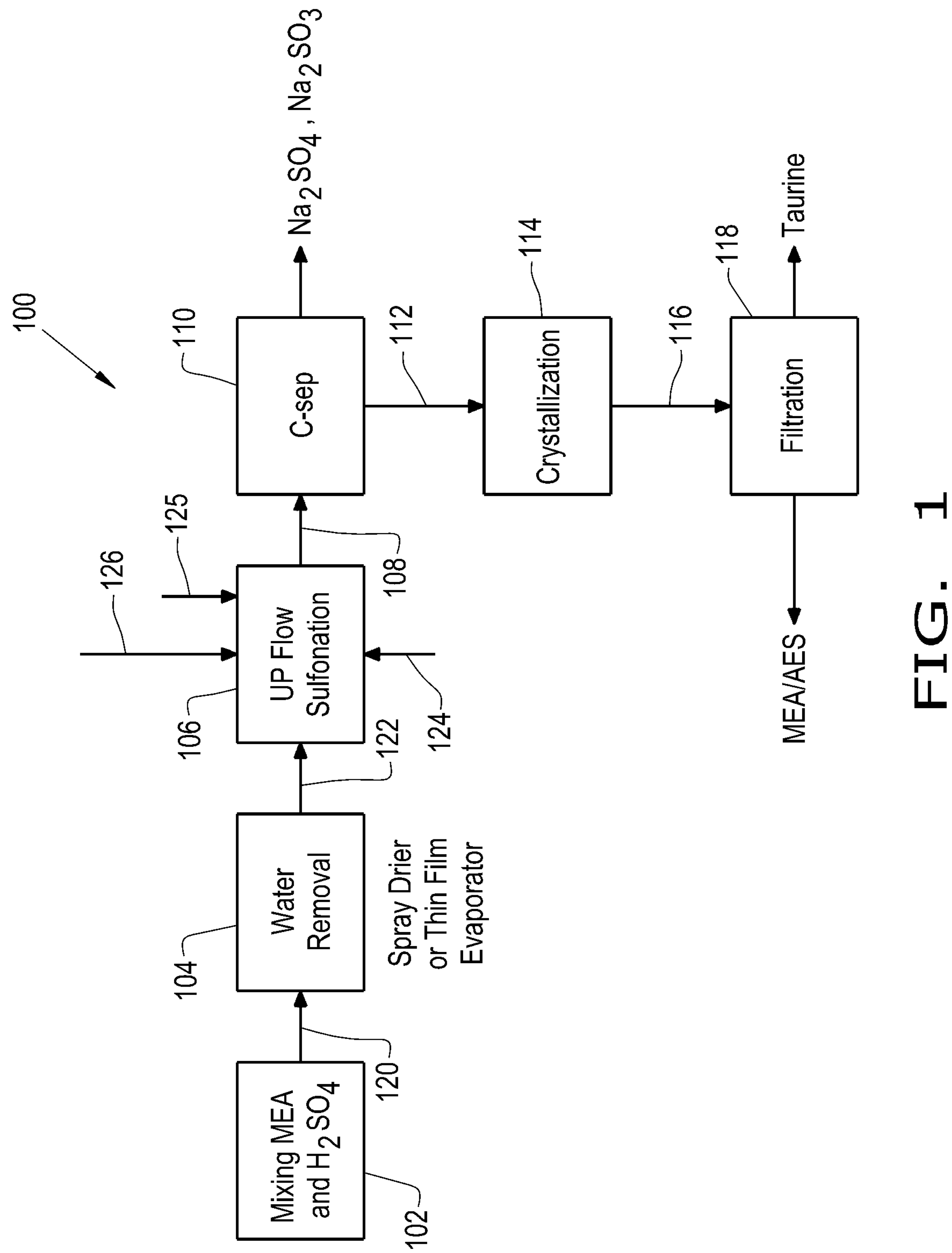
FIG. 1 is a process flow diagram of a continuous taurine production process in accordance with aspects of the invention.

FIG. 1 is a process flow diagram of an illustrative continuous taurine production process in accordance with aspects of the invention. As shown in FIG. 1, a continuous taurine manufacturing process 100 in one embodiment comprises a continuous first, esterification step 102 wherein monoethanolamine (MEA) and sulfuric acid ($H_2SO_4$) are continuously reacted, with at least some degree of concurrent water removal.

In certain embodiments, this concurrent water removal involves use of an inert particulate material that possesses the capability of receiving and removing water from the esterification step as it progresses. In other embodiments, this concurrent water removal involves carrying out some of the esterification in the course of removing water from the process by spray drying or thin film evaporation. In still other embodiments, the water removal involves both use of an inert particulate material as well as spray drying or thin film evaporation.

In terms of the use of an inert particulate material with an intrinsic water removal capability, this capability can be associated, for example, with a porous inert particulate material wherein the pores are such as to receive and hold water as the esterification reaction proceeds, or with a material which readily forms stable hydrates as the esterification reaction proceeds. The inert particulate material will also preferably be substantially insoluble in all of sulfuric acid, monoethanolamine and water under the conditions of both the esterification step and the subsequent sulfonation step, so that the material can be readily separated by from the desired taurine product following the sulfonation step. A particularly suitable inert particulate material having these qualities is (anhydrous) sodium sulfate, which forms a stable decahydrate under the conditions of the esterification step and which is beneficially readily separable from the taurine, as is already known in the art.

The continuous esterification step 102 may, in respect of certain embodiments of using such a material for water removal, be initiated in advance of the introduction of the inert particulate material (or in advance of the initiation of contact with the inert particulate material by MEA, sulfuric acid or both) and then continued in the presence of the inert particulate material and with the associated water removal provided by the material, or in other embodiments, the inert particulate material can be introduced as either or both of monoethanolamine and sulfuric acid are provided to the esterification step 102, for example, in the form of a slurry of sodium sulfate in MEA.

In the same fashion, it will be understood that a water removal step 104 whereby water is removed as the esterification step progresses can occur to a degree concurrent with the esterification step 102 as well as following the substantial completion of the esterification reaction and the formation of the 2-aminoethanol hydrogen sulfate ester intermediate, or can occur substantially concurrently with the esterification step 102. Thus, where water removal step 104 is performed using a spray dryer or thin film evaporator in addition to the inert particulate material, in certain embodiments, the spray drying or thin film evaporation follows some reaction of monoethanolamine with sulfuric acid in the presence of the inert particulate material to form 2-aminoethanol hydrogen sulfate ester (in some upstream vessel as suggested by effluent 120 or even in the combining of monoethanolamine and sulfuric acid for spraying into a spray dryer via a nozzle which is amenable to the introduction of a liquid including an inert particulate solid), while in other embodiments the reaction of monoethanolamine with sulfuric acid in the presence of the inert particulate material will be carried out substantially in the spray dryer or thin film evaporator—in effect, carrying out esterification step 102 and water removal step 104 concurrently, and eliminating a separate effluent 120 from esterification step 102. An example of the latter group of embodiments would involve spraying in (in the context of a spray dryer) or otherwise supplying (in the context of a thin film evaporator) the MEA and sulfuric acid separately—in certain embodiments including the inert particulate material such as sodium sulfate with the MEA or sulfuric acid to form a slurry which is sprayed into the spray dryer or supplied to the thin film evaporator.

Those of skill in the art will appreciate from the foregoing that there will be a number of different embodiments that could be considered for accomplishing the reaction of monoethanolamine and sulfuric acid with at least some assistance in removing water from the process by means of an inert particulate material with water removing capabilities, in terms of when and how the inert particulate material is introduced, whether or not additional water removal measures are undertaken, by what manner (e.g., spray drying, thin film evaporation or by other means) and when in relation to the formation of the 2-aminoethanol hydrogen sulfate ester, and that these various embodiments will have different advantages and disadvantages relative to one another. Ideally, however, the inert particulate material in combination with any other water removal device or means removes enough water to enable full conversion to the desired 2-aminoethanol hydrogen sulfate ester intermediate in the form of effluent 122, provide an AES intermediate that is free-flowing and not prone to fouling the walls of a spray dryer or downstream equipment leading to the sulfonation step as well as beneficially reduce water removal loads in the refining and purification of the finished taurine product, following the sulfonation step.

After water removal step 104, effluent 122 comprising AES is then sent to a second, sulfonation step 106, wherein the AES is continuously sulfonated by reaction with a sulfite, bisulfite or combination of these in the presence of carbon dioxide, a carbonate, bicarbonate or a combination of any of these in a second, sulfonation step to continuously produce a taurine product. In this regard, we have discovered that the addition of carbon dioxide, a carbonate, a bicarbonate or a combination of any of these to a reaction mixture of 2-aminoethanol hydrogen sulfate ester (AES) and sulfite, bisulfite or combination of these dramatically increases taurine yield from the second, sulfonation step and decreases production of undesirable taurine by-products, such as, for example, N-2-aminoethyl-2-aminoethanesulfonic acid, depicted in formula (i) below.

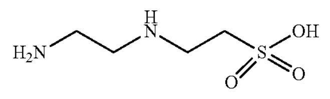

(i)

The carbonate or bicarbonate may be any suitable carbonate or bicarbonate, such as soda ash. In an embodiment, a convenient inexpensive salt such as sodium carbonate ($Na_2CO_3$) or sodium bicarbonate ($NaHCO_3$) may be the source of carbonate/bicarbonate. Carbon dioxide as an alternative avoids the addition of an accompanying counterion that comes with the introduction of a carbonate or bicarbonate, and may be considered preferable for that reason by those of skill in the art.

The aqueous solution of sulfite may in certain embodiments be sodium sulfite or sodium bisulfite. In certain embodiments where a bisulfite is used, a base may be added to raise the pH of the reaction mixture to a range of about 7.0 to about 8.3. In an embodiment, the base is chosen from an alkali metal hydroxide (e.g., sodium hydroxide) or ammonium hydroxide, or a combination thereof.

In certain embodiments, a process comprises continuously adding a first stream, a second stream, and a third stream to a sulfonation vessel, wherein the first stream comprises AES, wherein the second stream comprises carbon dioxide, a carbonate, a bicarbonate or a combination of any of these, and wherein the third stream comprises an aqueous solution of a sulfite, bisulfite or combination of these.

In certain embodiments, the process comprises continuously mixing the first, second and third streams in the sulfonation vessel, thus producing a mixture. In some embodiments, the process comprises continuously subjecting the mixture to heat. In certain embodiments, the step of continuously subjecting the mixture to heat is performed in the presence of an inert gas. In some embodiments, the process further comprises subjecting the mixture to a pressure greater than autogenous pressure. In certain embodiments, the 2-aminoethanol hydrogen sulfate ester (AES) has a residence time in the sulfonation vessel of no more than four (4) hours. In an embodiment, the AES has a residence time in the sulfonation vessel of no more than two (2) hours, the heat is a temperature of 110-155 degrees C., and the mixture is subjected to a pressure of at least 100 psi. In certain embodiments, the sulfite is chosen from at least one of a sulfite or a bisulfite, or combination thereof, e.g., sodium sulfite, sodium bisulfite, or combination thereof. In an aspect, the process results in a taurine yield of at least 80%.

From one perspective, an advantage of adding the carbon dioxide, carbonate and/or bicarbonate to the reaction mixture of AES and sulfite and/or bisulfite is that the amount of sulfite and/or bisulfite required to obtain at least the same taurine yield in the same process is reduced as compared to that required in the absence of adding the carbon dioxide, carbonate and/or bicarbonate to the reaction mixture of AES and sulfite and/or bisulfite. In an embodiment, the adding of the carbon dioxide, carbonate and/or bicarbonate to the reaction mixture of AES and sulfite reduces the mole ratio of sulfite to AES from about 1.8 and greater to about 1.2-1.3 to obtain at least the same taurine yield in the same process. In an embodiment, the adding of the carbon dioxide, carbonate and/or bicarbonate to the reaction mixture of AES and sulfite and/or bisulfite reduces by about 28% the mole ratio of sulfite to AES required to obtain at least the same taurine yield in the same process but absent the carbon dioxide, carbonate and/or bicarbonate addition.

In certain embodiments, the first stream comprised of AES and the second stream comprising carbon dioxide, a carbonate, a bicarbonate or a combination of any of these are mixed in a first part of the sulfonation vessel, with the third stream comprised of an aqueous solution of a sulfite, bisulfite or a combination thereof being mixed with the materials from the first part of the sulfonation vessel in a second part of the sulfonation vessel with heating to form taurine.

In an embodiment, in addition to forming taurine, a carbamate may be formed. An example of carbamate is 2-(Carboxyamino) ethanesulfonic acid and is depicted in formula (ii) below.

(ii)

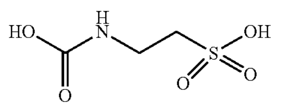

In an embodiment, the carbamate in formula (ii) may be converted to taurine with the addition of an acid, such as concentrated sulfuric acid.

In an embodiment, pH adjustment (e.g., by acidulation as just described) in the sulfonation vessel provides increased taurine yield and less production of undesirable taurine by-products compared to carrying out the second, sulfonation step with no pH adjustment.

The inert gas may be any suitable inert gas, including but not limited to nitrogen, helium, argon, and combinations thereof. In a preferred embodiment, the inert gas is nitrogen. In certain embodiments, the second, sulfonation step is conducted at a temperature of at least 115 degrees Celsius and at a pressure greater than autogenous pressure. The presence of the inert gas subjects the mixture to the pressure greater than autogenous pressure. In certain embodiments, the sulfonation step is conducted at a pressure of at least 50 psi, more preferably at least 100 psi, and even more preferably at least 200 psi, and results in a taurine yield of at least 80%. More preferably, by means of the carbonate and/or bicarbonate addition and by means of the pH adjustment prescribed herein for the second, sulfonation step in certain embodiments, at least a 95% AES conversion to taurine and a yield of at least 80% can be realized after a residence time of no more than four (4) hours in the vessel. This residence time of no more than four (4) hours is substantially less than the period of time normally required for sulfonation in conventional MEA methods. In certain embodiments, the AES has a residence time of no more than two (2) hours in the sulfonation vessel.

During the sulfonation step 106, sodium sulfate ($Na_2SO_4$) may also be formed, which as mentioned previously can be recycled (typically in part compared to the overall amount of sodium sulfate formed) to the first, esterification step 102 for use as an inert particulate material having water removal capabilities.

Sulfonation step 106 may comprise using an upflow or downflow sulfonation reactor wherein effluent 122 comprising AES is continuously pumped to the bottom or top of the sulfonation reactor, while a stream 124 comprising aqueous sodium sulfite, bisulfite or a combination is continuously supplied to the bottom or top of the sulfonation reactor and a stream 125 comprising one or more of carbon dioxide, a carbonate, e.g., soda ash, and a bicarbonate in water is continuously supplied to the bottom or top of the sulfonation reactor. The sulfonation reactor may be sealed with a pressure head with an inert gas 126 (e.g., nitrogen gas). Sulfonation step 106 comprises continuously subjecting the mixture of AES, sulfite and/or bisulfite, and carbon dioxide, carbonate and/or bicarbonate to heat in the presence of the inert gas. The heat may be a predetermined reaction temperature. In certain embodiments, the mixture of AES, sulfite or bisulfite, and carbon dioxide, carbonate and/or bicarbonate is continuously subjected to a pressure greater than autogenous pressure. In certain embodiments, the pressure may be at least 200 psi inert gas (e.g., nitrogen) and the reaction temperature maintained in the sulfonation vessel may be at least 115 degrees Celsius, in other embodiments being at least 120 degrees Celsius up to 155 degrees Celsius. In a more preferred embodiment, the sulfonation step may be carried out at from 140 to 155 degrees Celsius.

Effluent 108 from sulfonation step 106 may then in certain embodiments be processed to remove the sodium sulfate, by means and methods known in the art. The insolubility of sodium sulfate in water lends itself, in particular, to a recovery of the sodium sulfate by precipitation, but other means may be conceived and used by those familiar with the manufacture of taurine and with the properties of sodium sulfate. The water of hydration acquired by the sodium sulfate in the esterification step 102 is then removed with heating for at least a recycle portion of the sodium sulfate, and the preferably anhydrous sodium sulfate in the recycle portion is then recycled back to the esterification step 102.

Where sodium sulfate is used as an inert particulate material in the esterification step 102, then sodium sulfite is understandably preferably recovered separately from the sodium sulfate, for example, by a chromatography step 110.

Effluent 112 from chromatography step 110 comprises taurine, and in certain embodiments the effluent 112 may be conveyed to crystallization step 114 to recover the taurine. The crystallization step 114 may comprise cooling effluent 112 from an elevated temperature, e.g., about 100° C., to a lower temperature, e.g., about 28° C. Crystallization step 114 may be preceded by a water removal step (not shown in FIG. 1) wherein further water is removed from effluent 112, e.g., by distillation, thereby concentrating the amount of taurine in effluent 112 prior to crystallization.

Effluent 116 from crystallization step 114 comprises crystallized taurine and may be conveyed to filtration step 118. In filtration step 118, crystallized taurine is separated from any unreacted AES.

Alternatively, effluent 112 may in certain embodiments be conveyed directly to the filtration step 118, with additional water removal again optionally preceding a cooling of the effluent 112 to cause the taurine to precipitate as a filterable mass from any unreacted AES from the sulfonation step 106.

Figure 2:
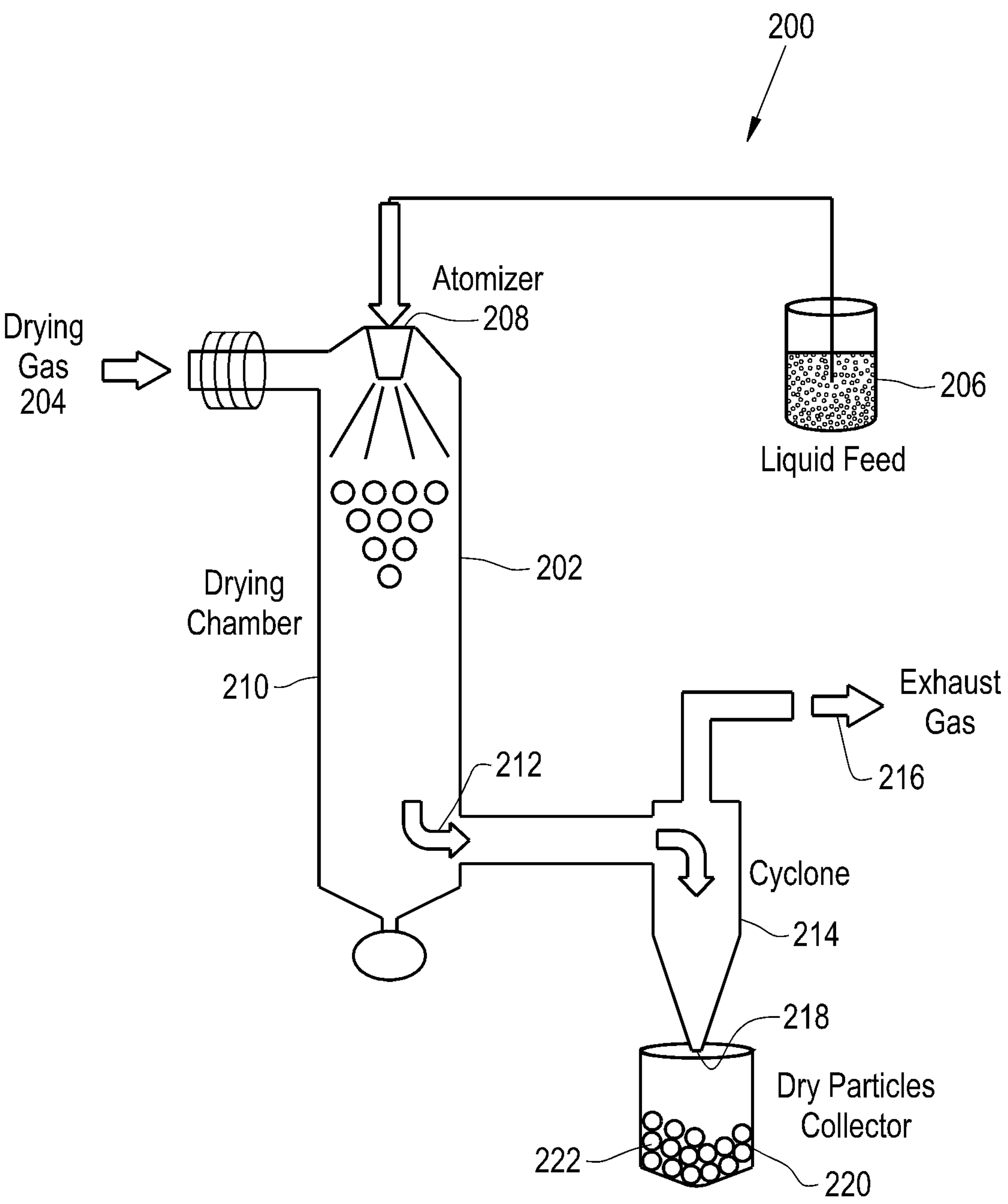
FIG. 2 depicts a drying apparatus for water removal in accordance with aspects of the invention.

Returning now to further consider particular embodiments of concurrent water removal in the first, esterification step (in those preferred embodiments wherein such concurrent water removal is employed), FIG. 2 depicts a purely illustrative drying apparatus 200 for accomplishing an additional measure of water removal in certain embodiments of. Drying apparatus 200 comprises spray dryer 202. Drying apparatus 200 comprises drying gas 204. Drying gas 204 may be an inert gas, e.g., nitrogen. Liquid feed 206 may be the same as effluent 120 shown in FIG. 1, though as already mentioned, in other embodiments a mixture of substantially unreacted monoethanolamine and sulfuric acid can be supplied directly to the spray dryer 202 (in an embodiment, with inert particulate material such as sodium sulfate being included in one or the other or both in a slurry form) or MEA, sulfuric acid or both may be independently supplied to the spray dryer in any manner known to those in the spray drying art—in co-current or countercurrent flows.

Spray dryer 202 may comprise drying chamber 210 and an atomizer 208 configured to atomize a liquid feed 206. Effluent 212 from spray dryer 202 may be conveyed to cyclone 214. In cyclone 214, exhaust gas 216 is separated from effluent 222. Effluent 222 exits cyclone 214 through opening 218. Effluent 222, comprising unreacted AES, may be collected in a collector 220. Thus, effluent 222 comprising AES has less water than liquid feed 206.

Figure 3:
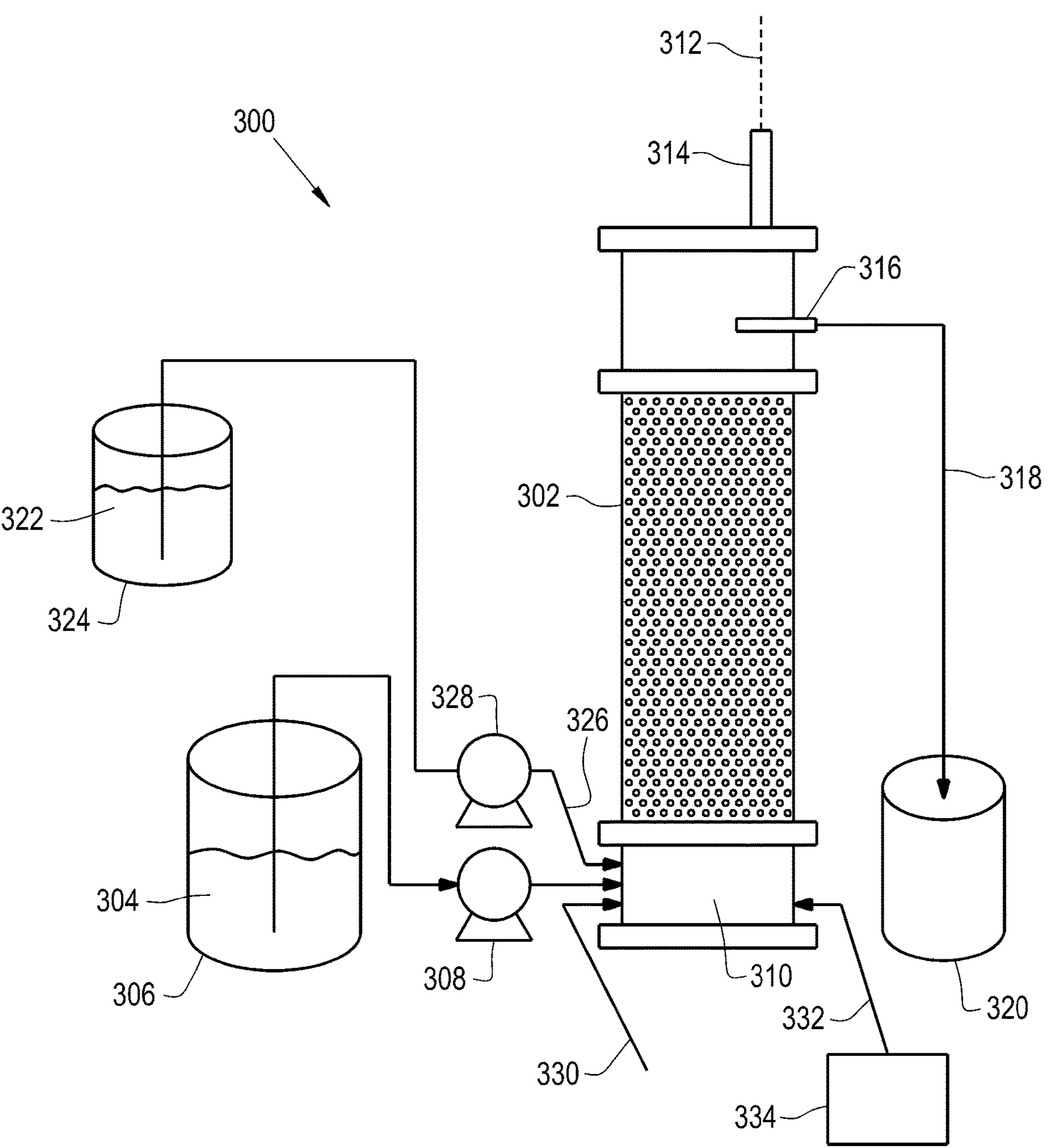
FIG. 3 depicts an apparatus for sulfonation in accordance with aspects of the invention.

FIG. 3 depicts a particular apparatus 300 for sulfonation step 106 shown in FIG. 1 in accordance with aspects of the invention, using carbon dioxide, carbonate and/or bicarbonate addition in the sulfonation step 106. As shown in FIG. 3, apparatus 300 may comprise an upflow sulfonation reactor 302. Those skilled the art having the benefit of the present disclosure will recognize that the sulfonation reactor may also be a downflow sulfonation reactor. Feed 304 in feed vessel 306 may be degassed by an inert gas prior to being conveyed out of feed vessel 306. The inert gas may be any suitable inert gas, including but not limited to nitrogen, helium, argon, and combinations thereof. In a preferred embodiment, the inert gas is nitrogen. Feed 304 is continuously conveyed out of feed vessel 306 by pump 308 to bottom 310 of upflow sulfonation reactor 302. Feed 304 may be the same as effluent 222 shown in FIG. 2. Thus, feed 304 comprises AES. As shown in FIG. 3, AES may be continuously pumped to the bottom of the sulfonation reactor 302. In sulfonation reactor 302, AES reacts with sulfite and/or bisulfite present in the sulfonation reactor 302 to form taurine.

Aqueous sulfite and/or bisulfite 322, e.g., aqueous sodium sulfite and/or aqueous sodium bisulfite, in vessel 324 may be degassed by an inert gas prior to being conveyed out of vessel 324. The inert gas may be any suitable inert gas, including but not limited to nitrogen, helium, argon, and combinations thereof. In a preferred embodiment, the inert gas is nitrogen. Aqueous sulfite and/or bisulfite 322 is continuously conveyed out of vessel 324 as stream 326 by pump 328 to bottom 310 of upflow sulfonation reactor 302.

In the illustrated sulfonation apparatus 300, carbon dioxide, carbonate and/or bicarbonate stream 332 is continuously conveyed out of a source 334 of the carbon dioxide, carbonate and/or bicarbonate to the bottom 310 of upflow sulfonation reactor 302. Where carbon dioxide is used in the apparatus 300, the source 334 can be any suitable carbon dioxide source, e.g., a pressurized tank of carbon dioxide, a compressor conveying carbon dioxide or a process stream of carbon dioxide, Sulfonation reactor 302 may be sealed with a pressure head with an inert gas, e.g., inert gas 330. Sulfonation reactor 302 may be operated by heating the reaction mixture of AES and aqueous sulfite and/or bisulfite at a reaction temperature and under a reaction pressure, e.g., a reaction pressure of at least 200 psi inert gas (e.g., nitrogen). The reaction temperature may be at least 110 degrees Celsius. In an embodiment, the reaction temperature may be at least 120 degrees Celsius. In a preferred embodiment, the reaction temperature may be 120-155 degrees Celsius. In a more preferred embodiment, the reaction temperature may be 140-155 degrees Celsius. Via conduit 316, effluent 318 may be collected in vessel 320. Thus, effluent 318 comprises taurine and may also comprise $Na_2SO_4$ and $Na_2SO_3$. Exhaust gas 312 comprising inert gas may exit sulfonation reactor 302 through conduit 314 as may be desired, e.g., to purge materials in sulfonation reactor, or maintain a predetermined pressure in the sulfonation reactor 302.

Figure 4:
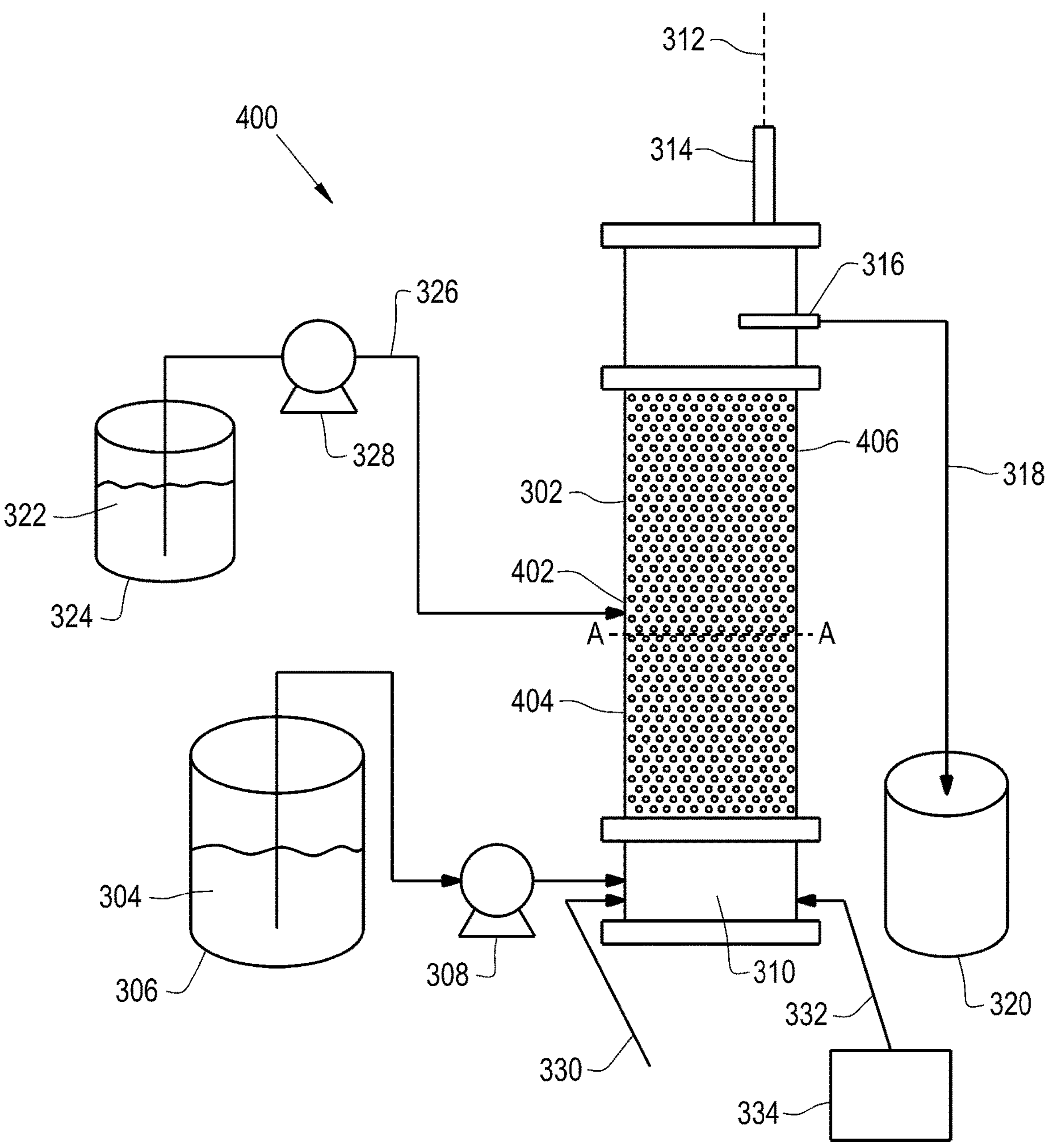
FIG. 4 depicts an apparatus for sulfonation in accordance with aspects of the invention.

FIG. 4 depicts an alternative sulfonation apparatus 400 for performing a sulfonation step 106 using carbon dioxide, carbonate and/or bicarbonate addition. Apparatus 400 is the same as apparatus 300 shown FIG. 3, with the exception that aqueous sulfite and/or bisulfite stream 326 is continuously conveyed by pump 328 to an upper part 406 of upflow sulfonation reactor 302 through inlet 402, rather than to the bottom 310 of upflow sulfonation reactor 302. Without being bound by theory, AES of feed 304 may react with carbon dioxide, carbonate and/or bicarbonate 332 to form a carbamate intermediate as previously mentioned, in lower part 404 of upflow sulfonation reactor 302. As shown in FIG. 4, lower part 404 is below dashed line A-A and upper part 406 is above dashed line A-A. In upper part 406, aqueous sulfite and/or bisulfite of stream 326 reacts with materials from lower part 404 to form taurine.

Figure 5:
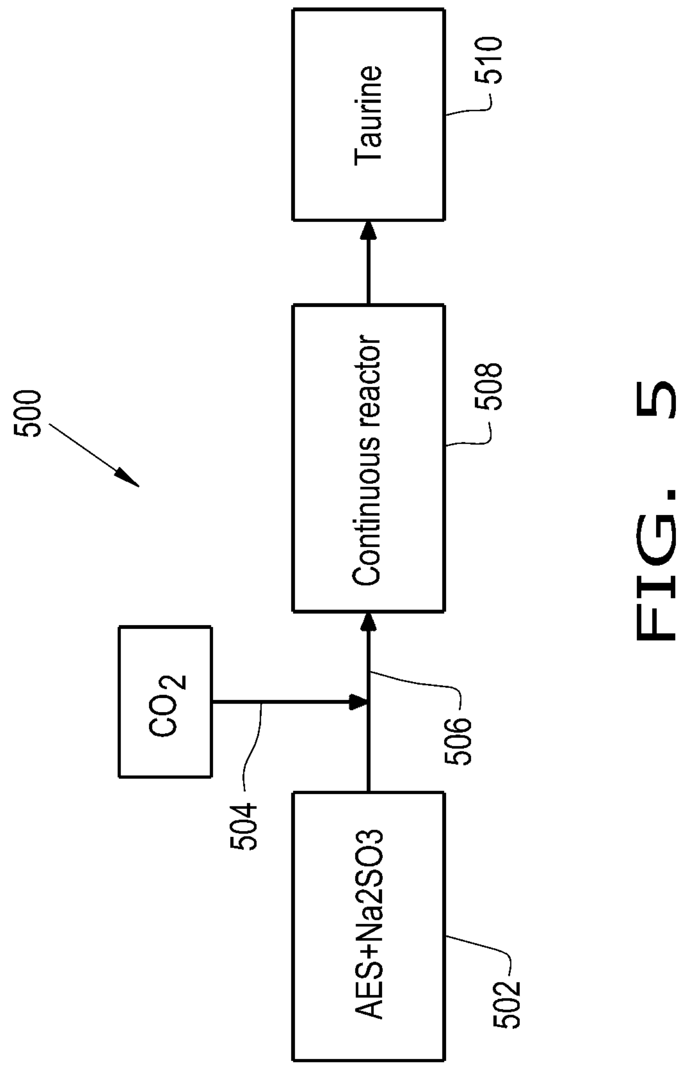
FIG. 5 depicts a process flow diagram of a continuous taurine production process using carbon dioxide in the second, sulfonation step.

FIG. 5 depicts a process flow diagram of a continuous taurine production process in accordance with aspects of the invention. As shown in FIG. 5, a continuous taurine manufacturing process 500 comprises providing a mixture 502 of AES and a sulfite and/or bisulfite and combining the same with stream 504 of carbon dioxide to form a sulfonation reaction mixture 506, then conveying the mixture 506 to a reactor 508 wherein taurine 510 is continuously formed from the mixture 506. Continuous reactor 508 may be the same as the sulfonation reactor 302 in FIGS. 3 and 4, and may thus be an upflow or downflow reactor. An inert gas, such as the inert gas 330 in FIG. 3, may be conveyed to reactor 508 and subject the sulfonation reaction mixture 506 to a pressure equal to or greater the autogenous pressure of the reaction mixture 506 at the reaction temperature prevailing in the reactor 508.

Table 1 summarizes the differences in the sulfonation steps of our process as compared to a traditional or conventional MEA method not using carbon dioxide, carbonate and/or bicarbonate addition, according to our experience with our method and our experience with and understanding of a typical, traditional or conventional method. In Table 1, the undesirable taurine by-products include specifically N-2-aminoethyl-2-aminoethanesulfonic acid, which is seen in a conventional MEA process but which we have not detected in taurine produced according to our method.

TABLE 1

| | Conventional MEA process | Process with carbon dioxide, carbonate and/or bicarbonate addition |
|---|---|---|
| Taurine yield % | 49-60% | >75% |
| Time, hours | 40-60 | <1 |
| Undesirable taurine by-products | Yes | No |
| Molar ratio, sulfite/AES | Equal or greater than 1.8 | 1.2-1.3 |
| Inert gas (e.g., nitrogen), inert gas pressure | No | Yes, 100 psi |
| pH | Neutral | 7.3-8.3 |
| Product color | Yellow | Colorless |
| Odor | Strong sulfur dioxide odor | Weak sulfur dioxide odor |
| Reactor | Batch | Continuous |

Table 2 shows the effect of various carbonate amounts on taurine yield from an illustrative second, sulfonation step conducted at 150 degrees Celsius over the course of an hour under 100 psi of nitrogen, using a 1.3:1 molar ratio of sodium bisulfite to AES. Sodium hydroxide was added in the molar ratios shown in Table 2 to raise the pH of the reaction mixture to the pH values shown in Table 2.

TABLE 2

| Carbonate: AES Molar Ratio | NaOH:SBS Molar Ratio | AES Conversion % | Taurine yield (mol %) | Feed pH |
|---|---|---|---|---|
| 0.4:1 | 0.49 | 100 | 71.8 | 7.1 |
| 0.6:1 | 0.72 | 100 | 76.7 | 7.7 |
| 0.7:1 | 0.77 | 100 | 81.5 | 7.9 |

The following examples further describe taurine synthesis in accordance with aspects of the present invention.

Example 1

A 300 cc Hasteloy autoclave reactor was charged with 35 g of $Na_2SO_3$, 150 g water, and heated to 50° C. to dissolve $Na_2SO_3$. After dissolving $Na_2SO_3$ in the water, 28 g of aminoethanol sulfate ester (AES) solid was added to autoclave reactor. The autoclave reactor was then sealed with a pressure head, purged three time with $N_2$ gas, then heated to 115° C. for sixteen (16) hours with 244 psi $N_2$ gas. After this time, the reaction was quenched by flash cooling in an ice bath. Once the thermocouple temperature read 20° C., the pressure head was removed, and liquid transferred to a storage vessel. The product was analyzed by LC and $^1H$, C13 NMR. Results from these analyses indicated a 100% AES conversion with 85% taurine yield.

Example 2

A 300 cc Hasteloy autoclave reactor was charged with 35 g of $Na_2SO_3$, 150 g water, and heated to 50° C. to dissolve $Na_2SO_3$. After dissolving $Na_2SO_3$ in the water, 28 g of aminoethanol sulfate ester (AES) solid was added to autoclave reactor. The autoclave reactor was then sealed with a pressure head, purged three time with $N_2$ gas, then heated to 115° C. for five (5) hours with 900 psi $N_2$ gas. After this time, the reaction was quenched by flash cooling in an ice bath. Once the thermocouple temperature read 20° C., the pressure head was removed, and liquid transferred to a storage vessel. The product was analyzed by LC and $^1H$, C13 NMR. Results from these analyses indicated that an 86% AES conversion with 82% taurine yield.

Example 3

A 250 ml round bottom flask was charged with 18 g of $Na_2SO_3$, 75 g water, and heated to 50° C. to dissolve $Na_2SO_3$. After dissolving $Na_2SO_3$ in the water, 14 g of aminoethanol sulfate ester (AES) solid was added to flask. The flask was refluxed at 115° C. for thirty (30) hours. After this time, the reaction was quenched by flash cooling in an ice bath. The product was analyzed by LC and $^1H$, C13 NMR. Results from these analyses indicated a 73% AES conversion with 68% taurine yield.

Example 4

A 300 cc Hasteloy autoclave reactor was charged with 35 g of $Na_2SO_3$, 150 g water, and heated to 50° C. to dissolve $Na_2SO_3$. After dissolving $Na_2SO_3$ in the water, 28 g of aminoethanol sulfate ester (AES) solid was added to reactor. The reactor was then sealed with a pressure head, purged three time with $N_2$ gas, then heated to 105° C. for six (6) hours with 200 psi $N_2$ gas. After this time, the reaction was quenched by flash cooling in an ice bath. Once the thermocouple temperature read 20° C., the pressure head was removed, and liquid transferred to a storage vessel. The product was analyzed by LC and $^1H$, $^{13}C$ NMR. Results from these analyses indicated a 62% AES conversion with 58% taurine yield.

Example 5

A 300 cc Hasteloy autoclave reactor was charged with 35 g of $Na_2SO_3$, 150 g water, and heated to 50° C. to dissolve $Na_2SO_3$. After dissolving $Na_2SO_3$ in the water, 28 g of aminoethanol sulfate ester (AES) solid was added to reactor. The reactor was then sealed with a pressure head, purged three time with $N_2$ gas, then heated to 115° C. for five (5) hours with 900 psi $N_2$ gas. After this time, the reaction was quenched by flash cooling in an ice bath. Once the thermocouple temperature read 20° C., the pressure head was removed, and liquid transferred to a storage vessel. The product was analyzed by LC and $^1H$, $^{13}C$ NMR. Results from these analyses indicated an 86% AES conversion with 81% taurine yield.

The above examples indicated that elevated temperature under pressure with an inert gas, such as $N_2$ gas, improves taurine yield and reduces the sulfonation reaction time. Example 3 had a sulfonation stage with a reaction time of thirty (30) hours and was not under pressure with $N_2$ gas. Examples 1, 2, 4, and 5, had much shorter sulfonation stages of either five (5) or (six) hours under pressure with $N_2$ gas.

Example 6

The following example demonstrates a method wherein a thin film evaporator is used to remove water. The thin film evaporator may be used for the water removal step 104 shown in FIG. 1. In accordance with reacting step 102 shown in FIG. 1, MEA (20 g) was charged into a 250 ml flask equipped with a stirrer and a thermometer. $H_2SO_4$ (36 g) was slowly added into the flask over 30 minutes employing a dropping funnel. The reactor used for the water removal step was placed in an ice/water bath during the initial $H_2SO_4$ addition to control the exothermic acid-base reaction. The above mixture was transferred to addition funnel and slowly added to the thin film evaporator, wherein the thin film evaporator had a temperature of 150° C. and 30 torr vacuum. White solids were collected and analyzed using NMR, HPLC analysis, and the resulting analysis demonstrated 95% purity and 85% recovery yield Example 7

The following example demonstrates a method wherein a spray dryer is used to remove water. The spray dryer may be used for the water removal step 104 shown in FIG. 1. In accordance with reacting step 102 shown in FIG. 1, In accordance with reacting step 102 shown in FIG. 1, MEA (12 g) was charged into a 250 ml flask equipped with a stirrer and a thermometer. $H_2SO_4$ (20 g) molar ratio (1:1) was slowly added into the flask over 30 minutes employing a dropping funnel.

The above mixture was transferred to a small bottle and slowly added to the spray dryer with the inlet and outlet temperatures indicated in Table 1 below, at a pumping rate at 3 mL/min and with a drying gas flow at 40 mm (473 L/hr). White solids were collected and analyzed using NMR, HPLC analysis, and the resulting analysis demonstrated 99% purity and 85.5% recovery yield as shown in Table 3 below.

TABLE 3

| Solid AES Recovery yield (wt %) | Purity (mol %) (Based on NMR) | Mass Balance mol % | Inlet temp. (° C.) | Outlet temp. (° C.) |
|---|---|---|---|---|
| 85.5 | 99.0 | 85.4 | 200 | 140 |

Example 8

Monoethanolamine (MEA) and sulfuric acid were premixed at a 1:1 molar ratio by slowly adding concentrated sulfuric acid into MEA in an ice bath. 3 wt % of anhydrous sodium sulfate was added to the premixed MEA and sulfuric acid mixture. This mixture was then fed into the same spray dryer used in Example 7 through a peristaltic pump and a spray nozzle for the generation of 2-aminoethanol hydrogen sulfate ester (AES). The inlet temperature of the spray dryer instrument was approximately 190 degrees Celsius. The drying gas was set at a gas flow rate of 470 L/h. The flow rate of the feed to the spray dryer was about 1.5 mL/min. The aspirator output of the instrument was set at 100% for all the experiments. After reaction, the generated 2-aminoethanol hydrogen sulfate (AES) was in the form of a more free-flowing, less tacky white solid as compared to that obtained in Example 7. The product was then collected and analyzed by $^1$H NMR and UPLC, and the addition of sodium sulfate was thereby confirmed as enabling improved yields of a comparable purity AES product to that obtained under the same circumstances but absent the addition of the anhydrous sodium sulfate.

Example 9

Monoethanolamine (MEA) and sulfuric acid were premixed at a 1:1 molar ratio by slowly adding concentrated sulfuric acid into the MEA in an ice bath. 3 wt % of anhydrous sodium sulfate was added to the premixed MEA and sulfuric acid mixture. This mixture was then fed into the spray dryer through a peristaltic pump and a spray nozzle for the generation of 2-aminoethanol hydrogen sulfate ester (AES). The inlet temperature of the spray dryer instrument was approximately 160 degrees Celsius. The drying gas was set at a gas flow rate of 470 L/h. The flow rate of the feed to the spray dryer was 1.5 mL/min. The aspirator output of the instrument was set at 100% for all the experiments. After reaction, the generated 2-aminoethanol hydrogen sulfate ester (AES) was again in the form of a more free flowing, less tacky white solid as compared to that obtained in Example 7. The product was then collected and analyzed by $^1$H NMR and UPLC, and the addition of sodium sulfate was thereby confirmed as enabling improved yields of a comparable purity AES product to that obtained under the same circumstances but absent the addition of the anhydrous sodium sulfate.

Example 10

In the same fashion as Examples 8 and 9, MEA and sulfuric acid were premixed at a 1:1 molar ratio by slowly adding concentrated sulfuric acid into MEA in an ice bath. 3 wt % of anhydrous sodium sulfate was again added to the premixed MEA and sulfuric acid mixture. This mixture was then fed into the spray dryer through a peristaltic pump and a spray nozzle for the generation of 2-aminoethanol hydrogen sulfate ester (AES). The inlet temperature of the spray dryer instrument was 170 degrees Celsius. The drying gas was supplied at 470 L/h. The feed was supplied to the spray nozzle at 1.5 mL/min. The aspirator output of the instrument was set at 100% for all the experiments. After reaction, the generated 2-aminoethanol hydrogen sulfate ester (AES) was in the form of a more free flowing, less tacky white solid as compared to that obtained in Example 7. The product was then collected and analyzed by $^1$H NMR and UPLC, and the addition of sodium sulfate was thereby confirmed as enabling improved yields of a comparable purity AES product to that obtained under the same circumstances but absent the addition of the anhydrous sodium sulfate.

Example 11

In the same fashion as Examples 8 and 9, MEA and sulfuric acid were premixed at a 1:1 molar ratio by slowly adding concentrated sulfuric acid into MEA in an ice bath. 3 wt % of anhydrous sodium sulfate was again added to the premixed MEA and sulfuric acid mixture. This mixture was then fed into the spray dryer through a peristaltic pump and a spray nozzle for the generation of 2-aminoethanol hydrogen sulfate ester (AES). The inlet temperature of the spray dryer instrument was 180 degrees Celsius. The drying gas was supplied at 470 L/h. The feed was supplied to the spray nozzle at 1.5 mL/min. The aspirator output of the instrument was set at 100% for all the experiments. After reaction, the generated 2-aminoethanol hydrogen sulfate ester (AES) was in the form of a more free flowing, less tacky white solid as compared to that obtained in Example 7. The product was then collected and analyzed by $^1$H NMR and UPLC, and the addition of sodium sulfate was thereby confirmed as enabling improved yields of a comparable purity AES product to that obtained under the same circumstances but absent the addition of the anhydrous sodium sulfate.

Example 12

In the same fashion as Examples 8 and 9, MEA and sulfuric acid were premixed at a 1:1 molar ratio by slowly adding concentrated sulfuric acid into MEA in an ice bath. 3 wt % of anhydrous sodium sulfate was again added to the premixed MEA and sulfuric acid mixture. This mixture was then fed into the spray dryer through a peristaltic pump and a spray nozzle for the generation of 2-aminoethanol hydrogen sulfate ester (AES). The inlet temperature of the spray dryer instrument was 200 degrees Celsius. The drying gas was supplied at 470 L/h. The feed was supplied to the spray nozzle at 1.5 mL/min. The aspirator output of the instrument was set at 100% for all the experiments. After reaction, the generated 2-aminoethanol hydrogen sulfate ester (AES) was in the form of a more free flowing, less tacky white solid as compared to that obtained in Example 7. The product was then collected and analyzed by $^1$H NMR and UPLC, and the addition of sodium sulfate was thereby confirmed as enabling improved yields of a comparable purity AES product to that obtained under the same circumstances but absent the addition of the anhydrous sodium sulfate.

Example 13

The following example demonstrates a method with up flow sulfonation.

30 cc reactors were built with stainless steel with bodies and an internal diameter (ID) of 0.61 inches. The reactors are jacketed and are heated with circulating oil. Reactor temperatures are monitored via an internal thermowell ⅛" with a 1/16" thermocouple that can slide up and down to monitor peak temperature. The temperature of the jacket is monitored by measuring the oil temperature just before it enters the jacket. The temperatures of the reactors are controlled by adjusting the oil temperature. The inlets of the reactors are attached to an Isco dual piston pump and mass flow controllers for supplying gases. The outlet was attached to a condenser kept at 5° C. by a chiller unit. The pressures of the reactors are controlled using a dome loaded back pressure regulator (Mity Mite brand).

Experimental Conditions: Jacket Temperature=140° C.; Liquid Hourly Space Velocity (LHSV)=0.5 (i.e., two (2) hours); $N_2$ Flow=100 ml/min; up flow AES Concentration=10.6% by wt.; Sulfite/AES molar ratio=1.9; pH=6.8.

Products of the reaction were analyzed by HPLC. These analyses indicated 100% AES conversion with taurine yield at 83%.

Example 14

A 5-gallon autoclave reactor was charged with 5.7 kg of 40% sodium bisulfite ($NaHSO_3$), and 2.26 kg of AES in 7.5 kg of water, then 975 grams of NaOH was added to above mixture with stirring. To above mixture, 616 grams of soda ash was added to keep the solution pH at 8.1. The reactor was then sealed with a pressure head, purged three times with nitrogen, then heated to 150° C. for 45 minutes (0.75 hours) with 200 psi nitrogen. After this time, the reaction was quenched by flash cooling in an ice bath. Once the thermocouple temperature read 20 deg. Celsius, the pressure head was removed, and liquid transferred to a storage vessel. The product was analyzed by LC-MS. Results from these indicated 100% AES conversion with 82% yield of taurine.

Example 15

To 20 ml of the product from Example 14 was added a small amount (3 drops) of concentrated $H_2SO_4$; the product was analyzed with NMR 1H and 13C. There was no carbamate in the final product.

Example 16

A number of sulfonation experiments were carried out to demonstrate the effect of carbonate/bicarbonate addition for reducing the amount of time and/or the amount of sulfite/bisulfite needed to achieve a particular taurine yield (or achieving greater taurine yields and reduced byproducts as compared to what would be realized in the absence of carbonate/bicarbonate addition, while still achieving reductions in needed reaction time and/or in sulfite/bisulfite requirements), and these results are provided in Table 4 (FIG. 6) and discussed below.

In a typical reaction, 11.03 grams of 40 wt % sodium bisulfite (SBS) solution was added to a 75 mL Hastelloy Parr reactor. Various amounts of NaOH at different molar ratios compared to SBS (in the range of 0.5:1-1:1 of NaOH:SBS, using 0.85-1.70 g of NaOH) was dissolved in 20 grams of $H_2O$, and then added to SBS solution. Various amounts of $Na_2CO_3$ at different molar ratios compared to AES (in the range of 0.1:1-0.8:1 of sodium carbonate ($Na_2CO_3$): AES, using 0.36-2.82 g $Na_2CO_3$) were measured and added to the mixture. After all of the $Na_2CO_3$ dissolved, 4.70 grams of AES was then added. The system was then heated to 60-65° C. to help accelerate the dissolving of AES. 70 mg of benzoic acid was added at last as an internal standard. The initial pH value of the feed was recorded, and a feed sample was taken for analysis using 1H NMR and 13C NMR. The reactor was then sealed, purged three times using nitrogen, and charged with 200 psi nitrogen before carrying out the sulfonation reaction. The reactions were performed at stirring speed 1000 rpm and a reaction temperature of 130 or 140° C. for two hours, or 150° C. for one hour. After reaction, the reactor was cooled down to room temperature, and the product mixture analyzed by 1H NMR and 13C NMR.

As shown in Example 15, addition of an acid, e.g., concentrated sulfuric acid, to a mixture of taurine and carbamate will convert the carbamate to taurine. Those skilled in the art having the benefit of the present disclosure will recognize that a similar addition of acid, such as concentrated sulfuric acid to the mixture of taurine and carbamate in Example 16, i.e., Samples 1-2, 4-13 and 15-43 made with carbonate (here, sodium carbonate) in accordance with aspects of the present invention, will convert the carbamate to taurine, resulting in a higher total taurine yield than without the addition of the carbonate. As shown above, the control Samples 3 and 14 (with no carbonate) had a total taurine yield (molar) of 60.2 and 64.2, respectively. Samples 1-2, 4-13 and 15-43 made with carbonate in accordance with aspects of the present invention had higher total taurine yield (molar), with the exception of Sample 19. The total taurine yield of Sample 19 is due to the low molar ratio of sulfite/AES of 0.92% (sodium bisulfite/AES), whereas the control Samples 3 and 14 had higher molar ratio of sulfite/AES of 1.3% (sodium bisulfite/AES) and 1.29% (sodium sulfite/AES), respectively.

Moreover, Samples 4-13 and 15-28 all had yields of the taurine byproduct N-2-aminoethyl-2-aminoethane sulfonic acid (molar) that were much lower than control Sample 3 that had a yield of 23% (molar) of the same undesirable taurine byproduct. Control Sample 14 was not measured for N-2-aminoethyl-2-aminoethane sulfonic acid. However, in view of the results of control Sample 3, it would be expected that control Sample 14 would give similar results and much higher yields of the undesirable byproduct than seen in Samples 4-13 and 15-28.

In this regard, as shown in Table 4, Samples 4-13 and 15-19 all had a yield of less than 1% of N-2-aminoethyl-2-aminoethane sulfonic acid (molar). As shown in Table 4, Samples 20-28 by contrast produced from 3.77% (Sample 25) to 7.99% (Sample 28) of this byproduct. Samples 1-2 and 29-43 were not measured. However, in view of the results of Samples 4-13, 15-19 and 20-28, it would be expected that Samples 1-2 and 29-43 would each have a similar low yield of the byproduct as all of these samples had carbonate addition.

Example 17

9.65 grams of 40 wt % sodium bisulfite (37 mmol) (SBS) solution was added to a 75 mL Hastelloy Parr reactor. An equal molar amount of NaOH was dissolved in 16.00 water, and then added to the SBS solution. 4.30 grams of AES (SBS/AES=1.3) was measured and added to the mixture. The system was purged with nitrogen three times, then 200 psi of carbon dioxide was added. The initial pH value of the feed was recorded, and a feed sample was taken for analysis using 1H NMR and 13C NMR. The sulfonation reaction was performed at stirring speed 1000 rpm and at a reaction temperature of 150° C. over the span of 1.5 hours. The reactor was cooled down to room temperature, and the product mixture analyzed by 1H NMR (Table 5) and 13C NMR.

TABLE 4

NMR analysis of taurine and other products

| | AES | MEA (molar) | Taurine yield (molar) | 2-(Carboxy amino) ethane sulfonic acid yield (molar) | N-2-Aminoethyl-2-aminoethane sulfonic acid (molar) | 2-oxazoli-dinone yield (molar) |
|---|---|---|---|---|---|---|
| Product | 0% | 20% | 58% | 0% | <1% | 20% |

As shown in Table 4, 0% AES was present in the product mixture, thus indicating that all AES present in the reactor was reacted. The MEA and 2-oxazolidinone in the product mixture may be recycled for upstream processing to yield more taurine. For example, MEA can be recycled back to reacting step 102 of FIG. 1 for making AES from MEA. The 2-oxazolidinone in the product mixture may be recycled to the sulfonation reactor for production of taurine. Less than 1% of the N-2-aminoethyl-2-aminoethanesulfonic acid byproduct was formed.

Those having skill in the art, with the knowledge gained from the present disclosure, will recognize that various changes can be made to the disclosed processes in attaining these and other advantages, without departing from the scope of the present disclosure. As such, it should be understood that the features of the disclosure are susceptible to modifications and/or substitutions. The specific embodiments illustrated and described herein are for illustrative purposes only, and not limiting of the invention as set forth in the appended claims.

What is claimed is:

1. A process for forming taurine, comprising:

reacting monoethanolamine with sulfuric acid to provide an 2-aminoethanol hydrogen sulfate ester product;

wherein the first, esterification step is accompanied by at least some concurrent water removal in producing the 2-aminoethanol hydrogen sulfate ester product;

combining the 2-aminoethanol hydrogen sulfate ester product with at least one of carbon dioxide, a carbonate, or a bicarbonate and with at least one of a sulfite or a bisulfite to form a sulfonation reaction mixture; and heating the sulfonation reaction mixture for a sufficient time to form a taurine product therefrom;

wherein the molar ratio of the carbon dioxide, carbonate, bicarbonate, or any combination thereof to the 2-aminoethanol hydrogen sulfate ester product in the sulfonation reaction mixture is equal to or greater than 0.1 and less than 1.0;

wherein the concurrent water removal is accomplished at least in part by use of both an inert particulate material that possesses the capability of receiving and removing water from the process and then removing the inert particulate material including its associated water from the process, and spray drying or thin film evaporation;

wherein the spray drying or thin film evaporation follows some reaction of monoethanolamine with sulfuric acid in the presence of the inert particulate material to form the 2-aminoethanol hydrogen sulfate ester product.

2. The process of claim 1, wherein a base is additionally present in the sulfonation reaction mixture.

3. The process of claim 1, wherein the 2-aminoethanol hydrogen sulfate ester product is combined with the at least one of carbon dioxide, a carbonate or bicarbonate before being combined with the at least one of a sulfite or bisulfite.

4. The process of claim 1, wherein the sulfonation reaction mixture is formed before the sulfonation reaction mixture undergoes heating sufficient to form taurine from the sulfonation reaction mixture.

5. The process of claim 1, wherein the sulfonation reaction mixture is formed concurrent with the application of sufficient heating to cause at least some of the 2-aminoethanol hydrogen sulfate ester product to be converted to taurine.

6. The process of claim 1, wherein the molar ratio of the sulfite, bisulfite or combination thereof to the 2-aminoethanol hydrogen sulfate ester product in the sulfonation reaction mixture is equal to or greater than 1.0 and less than about 3.0.

7. The process of claim 1, wherein the step of heating is performed in the presence of an inert gas.

8. The process of claim 7, wherein the inert gas is chosen from nitrogen, argon, helium, and combinations thereof.

9. The process of claim 1, further comprising subjecting the sulfonation reaction mixture to a pressure greater than autogenous pressure.

10. The process of claim 9, wherein the step of heating is performed in the presence of an inert gas, and the inert gas is present in a sufficient amount to subject the mixture to the pressure greater than autogenous pressure.

11. The process of claim 1, wherein the sulfonation reaction is carried out at a temperature of at least 110° C.

12. The process of claim 1, wherein the first, esterification step is conducted continuously to provide 2-aminoethanol hydrogen sulfate ester to the second, sulfonation step as a continuous sulfonation feed, and wherein the second, sulfonation step is likewise performed continuously on the continuous sulfonation feed to continuously produce taurine.

13. The process of claim 1, wherein the reaction of monoethanolamine with sulfuric acid in the presence of the inert particulate material is carried out substantially in the spray dryer or thin film evaporator and water is concurrently removed by means both of the inert particulate material and the spray drying or thin film evaporation.

14. The process of any of claim 1, further comprising separating $Na_2SO_4$ and $Na_2SO_3$ from the taurine product to provide a refined taurine product.

15. The process of claim 14, wherein the separating of $Na_2SO_4$ and $Na_2SO_3$ from the taurine product is performed at least in part by chromatography.

16. The process of claim 14, wherein the separating of $Na_2SO_4$ and $Na_2SO_3$ from the taurine product is performed at least in part by crystallization.

17. A process for forming taurine, comprising:

reacting monoethanolamine with sulfuric acid to provide an 2-aminoethanol hydrogen sulfate ester product;

combining the 2-aminoethanol hydrogen sulfate ester product with at least one of carbon dioxide, a carbonate, or a bicarbonate and with at least one of a sulfite or a bisulfite to form a sulfonation reaction mixture;

heating the sulfonation reaction mixture for a sufficient time to form a taurine product therefrom;

wherein the molar ratio of the carbon dioxide, carbonate, bicarbonate, or any combination thereof to the 2-aminoethanol hydrogen sulfate ester product in the sulfonation reaction mixture is equal to or greater than 0.1 and less than 1.0;

separating $Na_2SO_4$ and $Na_2SO_3$ from the taurine product to provide a refined taurine product; and further obtaining and recycling anhydrous $Na_2SO_4$ for use as an inert particulate material that possesses the capability of receiving and removing water from the process and then removing the inert particulate material including its associated water from the process, and spray drying or thin film evaporation.

18. The process of claim 17, wherein obtaining the anhydrous $Na_2SO_4$ for recycling comprises separating the $Na_2SO_4$ which has been removed from the taurine product from the $Na_2SO_3$ which has been removed from the taurine product, and then heating at least a portion of the $Na_2SO_4$ to remove any water of hydration associated therewith.

* * * * *